US008936797B2

(12) United States Patent
Blondel

(10) Patent No.: US 8,936,797 B2
(45) Date of Patent: Jan. 20, 2015

(54) POLYMERIC THICKENER COMPOSITION

(75) Inventor: Frédéric Blondel, Lezigneux (FR)

(73) Assignee: S.P.C.M. S.A., Andrezieux Boutheon (FR)

(*) Notice: Subject to any disclaimer, the term of this patent is extended or adjusted under 35 U.S.C. 154(b) by 447 days.

(21) Appl. No.: 12/734,530

(22) PCT Filed: Dec. 21, 2007

(86) PCT No.: PCT/EP2007/064513
§ 371 (c)(1),
(2), (4) Date: May 7, 2010

(87) PCT Pub. No.: WO2008/107034
PCT Pub. Date: Sep. 12, 2008

(65) Prior Publication Data
US 2010/0247473 A1 Sep. 30, 2010

(51) Int. Cl.
*A61K 8/02* (2006.01)
*A61K 8/73* (2006.01)
*A61Q 1/14* (2006.01)
*A61K 47/30* (2006.01)
*C08F 2/00* (2006.01)
*C08F 4/00* (2006.01)
*C08F 228/02* (2006.01)
*A61Q 19/00* (2006.01)
*A61K 8/81* (2006.01)
*C08F 220/56* (2006.01)
*C08F 220/58* (2006.01)
*A61Q 5/12* (2006.01)
*C08F 226/02* (2006.01)

(52) U.S. Cl.
CPC .............. *C08F 220/56* (2013.01); *A61Q 19/00* (2013.01); *A61K 8/8158* (2013.01); *C08F 220/58* (2013.01); *A61Q 1/14* (2013.01); *A61Q 5/12* (2013.01); *C08F 226/02* (2013.01)
USPC ..... 424/401; 424/70.17; 510/136; 514/772.3; 526/210; 526/211; 526/212; 526/225; 526/233; 526/287

(58) Field of Classification Search
USPC .................. 424/401, 47, 78.31, 70.13, 70.17; 510/136; 514/772.3; 526/210, 211, 526/212, 225, 233, 287
See application file for complete search history.

(56) References Cited

U.S. PATENT DOCUMENTS

| 4,698,404 | A | 10/1987 | Cramm et al. | |
| 4,859,458 | A * | 8/1989 | Salamone et al. | 424/70.15 |
| 4,950,725 | A | 8/1990 | Flesher et al. | |
| 5,100,660 | A | 3/1992 | Hawe et al. | |
| 5,856,370 | A * | 1/1999 | Chmelir | 521/128 |
| 6,673,861 | B2 * | 1/2004 | Tabacchi et al. | 524/458 |
| 2001/0049419 | A1 * | 12/2001 | Mallo et al. | 525/328.5 |
| 2010/0135917 | A1 * | 6/2010 | Winter et al. | 424/47 |

FOREIGN PATENT DOCUMENTS

| EP | 0343840 A2 | 11/1989 |
| EP | 0395282 A2 | 10/1990 |
| EP | 1 152 022 A1 | 11/2001 |
| EP | 1152022 A1 | 11/2001 |
| FR | 2 873 126 A | 1/2006 |
| WO | WO 2007/017441 * | 2/2007 |

OTHER PUBLICATIONS

The International Search Report for PCT Application No. PCT/EP2007/064513, Sep. 12, 2008.
The Written Opinion of the International Searching Authority for PCT Application No. PCT/EP2007/064513, Jun. 21, 2010.
Buchholz F L, entitled "Preparation Methods of Superabsorbent Polyacrylates," In: ACS Symposium Series 573, Superabsorbent Polymers, Science and Technology, Fredric L. Buchholz and Nicholas A. Peppas (eds.) Chapter 2, pp. 27-38, 1994, American Chemical Society, Washington DC.
Rouf C et al., entitled "Methacrylic-Allylic Interpenetrating Polymer Networks," In: Interpenetrating Polymer Networks, Advances in Chemistry Series 239, D. Klempner et al. (eds.) Chapter 5, pp. 143-156, 1994, American Chemical Society, Washington DC.

* cited by examiner

*Primary Examiner* — Blessing M Fubara
(74) *Attorney, Agent, or Firm* — Amster, Rothstein & Ebenstein LLP

(57) ABSTRACT

The present invention relates to polymeric thickener compositions comprising at least one water-swellable crosslinked copolymer, a process for preparing such compositions and their use as a thickener, e.g., in cosmetic, dermatologic, pharmaceutical or veterinary formulations. The water-swellable crosslinked copolymer according to the present invention is prepared from a mixture comprising (a) acrylamide, (b) an acrylamidoalkylsulfonic acid and/or a salt thereof and (c) an amine-based polyfunctional crosslinking agent comprising at least three allylic functions.

20 Claims, No Drawings

POLYMERIC THICKENER COMPOSITION

This is a U.S. national phase of PCT Application No. PCT/EP2007/064513, filed Dec. 21, 2007.

FIELD OF THE INVENTION

The present invention relates to polymeric thickener compositions comprising at least one water-swellable crosslinked copolymer, a process for preparing such compositions and their use as a thickener, e.g., in cosmetic, dermatologic, pharmaceutical or veterinary formulations.

BACKGROUND OF THE INVENTION

It is well known that, especially in the cosmetic industry, an important technical problem or requirement refers to the stability of water-containing formulations, such as cosmetic, dermatologic, pharmaceutical or veterinary formulations. In order to avoid the phases or components of corresponding formulations and emulsions to separate, water-containing formulations, like solutions, emulsions or suspensions are often thickened to higher viscosities by adding thickening agents or compositions. Ideally, these thickening agents should provide the desired thickening properties or viscosity stability over a wide pH range and also in the presence of electrolytes.

One approach for improving the stability of standard thickeners in the cosmetic field is based on the use of crosslinked polymers containing strongly acidic monomers. Crosslinked polymeric thickener compositions are, for example, suggested in EP 0 503 853. More precisely, a thickening composition containing a water-soluble polymeric material comprising units derived specifically from acrylamide and 2-acrylamido-2-methyl-propanesulfonic acid (with at least partially neutralized units) and N,N'-methylene-bis-acrylamide (used in a specific amount of from 0.06 to 1 millimole per mole of total monomer units) is described in EP 0 503 853.

OBJECTS AND SUMMARY OF THE INVENTION

Although numerous thickening agents are commercially available, there is still a strong demand for thickening agents or compositions which can be used for a multitude of applications and provide the desired viscosity stability over a wide pH range and also in the presence of electrolytes. For obvious reasons, thickening agents or composition to be used in, e.g., cosmetic or pharmaceutical applications also should not contain significant amounts of unhealthy or detrimental substances. Therefore, the use of (crosslinked) acrylamide-based polymeric thickening compositions may be considered disadvantageous in view of a significant residual monomer content observed in the compositions known in the prior art (although these compositions may provide other required properties, like smoothness).

Another problem relates to the oxidation stability of thickening agents or compositions described in the art. In the cosmetic field, the corresponding formulations often contain electrolytes which may compromise the stability of the thickeners. For example, most of the commercially available water-soluble crosslinking agents (such as methylene-bis-acrylamide) being used for the preparation of crosslinked polymeric thickening compositions are hydrolysable compounds (e.g. methylene-bis-acrylamide readily undergoes hydrolysis even in dilute acid solutions). Therefore, the resulting thickening agents or compositions often are sensitive to oxidation and to an acidic and/or alkaline medium.

In view of the foregoing observations, it would be advantageous to provide a thickening agent or composition which has the desired thickening properties or viscosity stability over a wide pH range and also in the presence of electrolytes. Furthermore, it would be advantageous if the thickening agent or composition has a low or negligible residual monomer content. Finally, it would also be advantageous if the thickening agent or composition provides the properties or characteristics which are especially desirable for cosmetic applications, like, e.g., the required smoothness and excellent feel.

Surprisingly, it has now been found that water-swellable crosslinked copolymers based on (a) acrylamide, (b) acrylamidoalkylsulfonic acids and/or its salts and (c) an amine-based polyfunctional crosslinking agent comprising at least three allylic functions are highly suitable as thickeners for, e.g., cosmetic, dermatologic, pharmaceutical and/or veterinary water-containing formulations. Therefore, according to one aspect of the present invention, a polymeric thickener composition is provided which comprises at least one water-swellable crosslinked copolymer derived from polymerization of a mixture comprising:
(a) acrylamide,
(b) acrylamidoalkylsulfonic acid and/or a salt thereof; and
(c) an amine-based polyfunctional crosslinking agent comprising at least three allylic functions.

The term "water-swellable" as used herein with respect to the inventive crosslinked copolymer is defined for the purposes of the invention as referring to water-insoluble copolymers, which optionally may contain a fraction of water-soluble polymers, wherein said fraction does not exceed 30% by weight, based on the copolymer.

According to further advantageous aspects of the present invention, the amine-based polyfunctional crosslinking agent is a tertiary amine, which is preferably selected from the group comprising triallylamine, trimethallylamine, allyldimethallylamine, diallylmethallylamine and salts of the foregoing compounds. Suitable salts of said tertiary amine include hydrochlorides, hydrobromides, hydroiodides, sulfates, sulfides, phosphates and phosphites.

According to another aspect of the invention, a process for making the inventive polymeric thickener is provided. The process involves the preparation of the water-swellable crosslinked copolymer from a mixture comprising (a) acrylamide, (b) acrylamidoalkylsulfonic acid and/or a salt thereof and (c) an amine-based polyfunctional crosslinking agent comprising at least three allylic functions, wherein the process is preferably carried out by inverse emulsion polymerization. The resulting product of this type of polymerization is called "inverse emulsion".

In still another aspect of the invention, the process for making a polymeric thickener involves the addition of the amine-based polyfunctional crosslinking agent to the polymerization mixture in an amount of more than 2 millimoles per mole of total monomer units, preferably in an amount of more than 2.2 millimoles per mole of total monomer units and even more preferred in amount of at least 2.4 millimoles per mole of total monomer units and up to 10 millimoles per mole of total monomer units.

According to another advantageous aspect of the present invention an inventive polymerization mixture having a pH-value in the range between 3 to 5, preferably between 3.5 and 4.5 and more preferably of about 4 is used for preparing the inventive crosslinked polymer. Furthermore, it was found that it is advantageous to use a polymerization mixture which comprises the amine-based polyfunctional crosslinking agent in the aforementioned amounts and which has a pH-value in the range between 3 to 5, preferably between 3.5 and 4.5, and more preferably of about 4.

According to a further aspect, the invention refers to the use of the inventive polymeric thickener composition as a thickener in cosmetic, dermatologic, pharmaceutical or veterinary water-containing formulations, which are preferably selected from the group comprising cleansing fluids, body creams, face creams and hair care compositions. The corresponding thickened formulations, according to the present invention, may contain the thickener composition in an amount of 0.1 to 5% by weight, preferably 0.5 to 4% by weight, especially preferably 0.7 to 3% by weight, based on the formulation.

The polymeric thickener composition according to the present invention according to another aspect of the present invention is used for improving and/or providing viscosity stability of cosmetic, dermatologic, pharmaceutical or veterinary water-containing formulations. The term "viscosity stability" as used herein means that a separation of the phases or components in water-containing formulations or emulsions is avoided over a wide pH range (e.g. from 1 to 12 or 3 to 9) and/or in the presence of electrolytes. An essential advantage of the use of the copolymers according to the invention is the high viscosity stability of the formulations even at an extremely acid pH, in contrast to the known products on the market.

These and other aspects of the present invention will be apparent from and elucidated with reference to the embodiments described hereinafter.

DETAILED DESCRIPTION OF EMBODIMENTS

According to one embodiment of the present invention, a polymeric thickener composition is provided, which comprises at least one water-swellable crosslinked copolymer obtained by polymerizing:
(a) acrylamide,
(b) an acrylamidoalkylsulfonic acid and/or a salt thereof; and
(c) an amine-based polyfunctional crosslinking agent comprising at least three allylic functions.

Surprisingly, it has now been found that water-swellable crosslinked copolymers based on (a) acrylamide, (b) acrylamidoalkylsulfonic acids and/or its salts and (c) an amine-based polyfunctional crosslinking agent comprising at least three allylic functions are highly suitable as thickeners for cosmetic, dermatologic, pharmaceutical or veterinary water-containing formulations. The resulting thickened formulations or emulsions, such as cleansing fluids, body and face creams, hair care compositions show excellent homogeneity and improved stability under different conditions and even after storage for several months after preparation of the formulation or composition.

According to another embodiment of the present invention, component (b) is an acrylamidoalkylsulfonic salt being selected from the group comprising ammonium salts and alkali metal salts. The free acid form of the acrylamidoalkylsulfonic monomer may be converted to the salt form by adding a suitable base, such as a hydroxide, that will provide the desired ammonium, amine or alkali metal ion in conventional manner.

The amine-based polyfunctional crosslinking agent according to the present invention is preferably a tertiary amine which may be selected from the group comprising triallylamine, trimethallylamine, allyldimethallylamine, diallylmethallylamine and salts of the foregoing compounds. According to one specific embodiment of the present invention, the amine-based polyfunctional crosslinking agent is a tertiary amine in the form of a salt being selected from the group comprising hydrochlorides, hydrobromides, hydroiodides, sulfates, sulfides, phosphates and phosphites. According to a further aspect of the invention, the amine-based polyfunctional crosslinking agent is a quaternary ammonium salt, preferably derived from alkylating a tertiary amine, which is preferably selected from the group comprising triallylamine, trimethallylamine, allyldimethallylamine and diallylmethallylamine. Suitable alkylating agents are well know to the skilled person. One example for an alkylated tertiary amine which may be used according to the present invention is an alkyltriallylammonium chloride, such as a methyl-, ethyl-, propyl- or butyltriallylammonium compound.

According to another embodiment of the present invention, the water-swellable crosslinked copolymer is obtained by polymerizing a mixture comprising 10 to 90, preferably 30 to 70 and particularly 40 to 60 moles of (a) acrylamide per mole of total monomer units and 10 to 90, preferably 30 to 70 and particularly 40 to 60 moles of (b) acrylamidoalkylsulfonic acid and/or a salt thereof per mole of total monomer units.

The inventive polymeric thickener composition according to yet another embodiment of the invention is obtained by adding a chain transfer agent to the polymerization mixture, wherein said chain transfer agent is preferably selected from the group comprising phosphate-type chain transfer agents, such as sodium hypophosphite, lower alcohols, such as methanol or isopropanol, thiol based chain transfer agent, such as 2-mercaptoethanol, sulfate type chain transfer agents, such as sodium methallylsulfonate, and mixtures of the foregoing agents. Typically the amount of chain transfer agent used ranges from about 0.001 wt. % to about 1% based on total weight of monomer.

According to a further aspect of the invention, a process for making a polymeric thickener composition containing at least one water-swellable crosslinked copolymer is provided, wherein said copolymer is prepared from a mixture comprising (a) acrylamide, (b) an acrylamidoalkylsulfonic acid and/or a salt thereof and (c) an amine-based polyfunctional crosslinking agent comprising at least three allylic functions. According to one advantageous aspect of the invention, the water-swellable crosslinked copolymer is prepared by inverse emulsion polymerization.

An inverse emulsion polymerization process usually comprises the following steps:
A) forming a water-in-oil emulsion of an aqueous solution of the monomers (a) and (b) in a hydrophobic phase, like an inert hydrocarbon liquid; and
B) polymerizing said monomers to form a polymer emulsion, optionally, by using a free radical generating catalyst to initiate the reaction, and controlling the temperature of the reaction mixture. The polymerization mixture may contain an emulsifier/primary surfactant at a concentration of about 0.5 to about 10%, by weight, of the total emulsion and the polymer may be produced in the presence of an effective chain transfer agent. The resulting inverse emulsion polymer composition according to the present invention may have an active polymer concentration of about 25 to about 75% by weight. The inverse emulsion composition according to the present invention may further comprise an inverting surfactant in a concentration of up to about 5 weight percent. The inverting surfactant may improve the crosslinked polymer's dissolution in water. Suitable inverting surfactants are those with an HLB of at least about 10, preferably 10 to 20, with an HLB of about 10 to about 15 being most preferred. Especially suitable are the non-ionic inverting surfactants. Typical "inverting agents" include fatty alcohol ethoxylates, fatty acid esters-sorbitan-polyethylene glycols-glycerol, alkyl polyglucosides, etc. Certain silicone compounds such as dimethicone copolyols can also be used.

According to the present invention, water-swellable (or swollen) polymers may be made by reverse phase polymerisation for instance as is described generally in U.S. Pat. No. 4,059,552.

The inventive crosslinked polymeric thickener compositions according to another aspect of the present invention may provide viscosities of greater than 18.000 cps at a pH of 3.0, preferably of greater than 19.000 cps and most preferably of greater than 20.000 cps and/or viscosities of greater than 25.000 cps at a pH of 3.

The inventive crosslinked polymeric thickener compositions and/or the process for making these thickeners provide several advantages: The water-swellable crosslinked copolymers according to the present invention may be incorporated at any temperature. The water-swellable crosslinked copolymers according to the present invention are efficient thickening and emulsifying polymers and, thus, are excellent stabilizing substances for compositions/formulations containing silicone, vegetable oils, ingredients in saline form or for compositions/formulations containing salts, or ingredients with a pH value lower than 6.

The process for making the inventive polymeric thickener comprises the step of adding an amine-based polyfunctional crosslinking agent. This crosslinking agent according to one embodiment of the invention is added in an amount of more than 2 millimoles per mole of total monomer units, preferably in an amount of more than 2.2 millimoles per mole of total monomer units and up to 10 millimoles per mole of total monomer units. For the realisation of the present invention, it has been unexpectedly observed (compared to standard practice using common crosslinking agent such as bifunctionnal methylene bis acrylamide) that the effect of the amine-based polyfunctional crosslinking agents having 3 or more allylic functions is not proportional. Rather, it was found according to the present invention that amounts of less than 2 millimoles per mole of total monomer units may give poor or lower thickening properties. Therefore, it is considered to be advantageous according to the present invention that the molar proportions of the said crosslinking agent during the polymerisation are more than 2 millimoles per mole of total monomer units, preferably more than 2.2 and even more preferred at least 2.4.

According to a further embodiment of the present invention, the inventive process is carried out as an inverse emulsion polymerization, wherein the aqueous phase containing the (a) acrylamide and the (b) acrylamidoalkylsulfonic acid preferably is dispersed in a hydrophobic phase. The hydrophobic phase may comprise an oil selected form the group comprising mineral oils, synthetic oils, vegetable oils, silicone oils and mixtures thereof.

According to one embodiment of the present invention, the ratio (% by weight) of aqueous phase to hydrophobic phase is between 60 to 40 and 80 to 20 and preferably is about 70 to 30.

It was found that it may be advantageous to use an emulsifying agent for carrying out the inventive process, wherein said emulsifying agent preferably should have an HLB value in the range of 3 to 8 and more preferably in the range of 4 to 6. HLB values in the aforementioned range provide suitable conditions for carrying out the inverse emulsion polymerization. According to a further aspect of the invention, said emulsifying agent is used in an amount of 2 to 5% by weight, based on the total emulsion mass.

The solid content in the thickener composition according to yet another embodiment of the invention is at least 40% by weight and preferably at least 50% by weight, based on the emulsion mass.

It is preferred according to the present invention that the pH value of the polymerization mixture, i.e. the pH of monomers phase, is in the range between 3 to 5 and more preferably is about 4. The pH of polymerization usually varies with the neutralization rate of the monomer's performing acidic function (which typically range from 5 to 95 percent). According to the present invention, it was surprisingly found that, the lower pH of polymerization is, the better the polymer thickening properties are (such as feel and stability), over a very wide range of pH values (1-13) while retaining a very strong and efficient thickening capability, even at a very acid pH value. Optimum thickening effects may be obtained when the pH of polymerization is between 3.5 and 4.5 or around 4, which is still a pH for which the problems of corrosion of industrial equipment are reduced.

The process for preparing the inventive crosslinked thickener composition may be advantageously carried out in the presence of a chain transfer agent, which preferably is selected from the group comprising phosphate-type chain transfer agents, such as sodium hypophosphite, lower alcohols, such as methanol or isopropanol, thiol based chain transfer agent, such as 2-mercaptoethanol and mixtures of the foregoing agents.

According to another aspect of the present invention, a polymeric thickener agent or composition is provided which is obtainable by the inventive process referred to above or described herein.

The polymeric thickener composition provided by the present invention according to another embodiment are used as a thickener in cosmetic, dermatologic, pharmaceutical or veterinary water-containing formulations, i.e. for increasing the viscosity in such formulations. According to the present invention, the thickener composition may be contained in a formulation being selected from the group comprising cleansing fluids, body creams, face creams and hair care compositions. The thickened formulation according to another embodiment of the invention comprises 0.1 to 5% by weight, preferably 0.5 to 4% by weight, especially preferably 0.7 to 3% by weight, based on the formulation, of the water-swellable crosslinked copolymer.

The polymeric thickener composition provided by the present invention may be used for providing and/or for improving the viscosity stability of cosmetic, dermatologic, pharmaceutical or veterinary water-containing formulations.

According to the present invention, it is also possible to concentrate (by heating under vacuum to remove excess water and organic solvent by distillation) or to isolate the crosslinked polymer by all known techniques. In particular, there are many processes for obtaining a powder on the basis of soluble polymer emulsions or ones which swell in water. These processes involve the isolation of the active matter from other constituents of the emulsion. Such processes include:

precipitation in a non-solvent medium such as acetone, methanol, and other polar solvents: simple filtration then permits isolation of the polymer particle, azeotropic distillation in the presence of an agglomerating agent and stabilizing polymer which makes it possible to obtain agglomerates which are easily isolated by filtration before drying of the particle is undertaken, "Spray drying", or drying by atomization or pulverization, which consists of creating a cloud of fine droplets of emulsion in a stream of hot air for a controlled period.

Even if the it would undoubtedly be technically possible to increase the proportion of water-soluble polymers, it has to be noted that the water-swellable crosslinked copolymers of the invention are characterized in that they are water insoluble (as determined by a metering method such as that described on page 8 of patent EP 0 343 840). They exhibit therefore a fraction of water-soluble polymers which is not exceeding 30 percent and is preferably below 20 percent in weight.

While the present invention has been described with respect to specific embodiments thereof, it will be recognized by those of ordinary skill in the art that many modifications, enhancements, and/or changes can be achieved without departing from the spirit and scope of the invention. Therefore, it is manifestly intended that the invention be limited only by the scope of the claims and equivalents thereof. The word "comprising" does not exclude the presence of elements or steps other than those listed in a claim. The word "a" or "an" preceding an element does not exclude the presence of a plurality of such elements. In the following, the invention is illustrated in view of certain examples. These examples are however in no way meant to limit the invention as to its scope, but rather serve to illustrate the invention by way of some of its exemplary embodiments.

EXAMPLES

A) Polymers

Each of the polymers described in the following section was obtained by inverse emulsion polymerization. In order to allow for a comparison of the resulting polymers or compositions, the polymerization conditions have been kept constant unless specified otherwise.

Polymerization Conditions:

A monomer solution is prepared comprising 120 g of a 50% aqueous acrylamide solution with 650 g of a 50% aqueous solution of 2-acrylamido-2-methylpropanesulfonic acid. Then the specified amount of crosslinking agent, 1.0 g of pentasodium diethylene triamine pentaecetate and 25 g of water are added. The pH of the aqueous monomer phase is obtained by adding sulphuric acid. The aqueous phase is transferred and homogenised into an oil phase (comprising ~12.3 g of sorbitan monooleate and ~250 g of a blend of white mineral oil) using a Silverson L2R mixer for 10 minutes at 7000 rpm. The system is cooled to 10° C. and spurged with nitrogen for 10 minutes. The polymerization is then started by adding in one shot 6 ml of 1% w/w ammonium persulfate in water and 0.2 ml/min of 1% aqueous solution of sodium metabisulfite. A temperature rise is observed and when no further rise occurs, the complete polymerisation is assumed. The so final liquid dispersion is rendered water dispersible by adding 40 g fatty ethoxylated alcohol (HLB>10).

From the resulting polymers, formulations in deionized water were prepared and tested with respect to their viscosity at different pH values. Furthermore, the residual monomer content was determined. The results are summarized in table 1 below.

TABLE 1

| water-swellable crosslinked copolymers | Polymer composition | | | 1) Viscosity n°1 cps | 2) Viscosity n°2 cps | 3) Residual acrylamide Monomer (ppm) |
|---|---|---|---|---|---|---|
| | AM | ATBS | Cross-linker | | | |
| X1 [pH = 4] | 40 | 60 | MBA 1 | 23500 | 18000 | 15 |
| X2 [pH = 4] | 40 | 60 | TAA 1 | 7500 | 6000 | 8 |
| X3 [pH = 6] | 40 | 60 | TAA 2.5 | 18000 | 15000 | 6 |
| P1 [pH = 3] | 40 | 60 | TAA 2.5 | 30500 | 21000 | 2 |
| P2 [pH = 4] | 50 | 50 | TAA 2.5 | 27000 | 20500 | 3 |

1) Viscosity n°1: viscosity measurement by means of a Brookfield RVT viscosimeter (in cps-units; at room temperature). Preparation of a 1 percent active polymer solution in deionized water.
2) Viscosity n°2: viscosity measurement at pH = 3 by means of a Brookfield RVT viscosimeter (in cps-units; at room temperature). Preparation of a 1 percent active polymer solution in deionized water, followed by adjustment of the pH value to between 2.9 and 3.1 by using 1N hydrochloric acid
[ ]: pH of polymerization
X: water-swellable crosslinked copolymer - comparative examples
P: water-swellable crosslinked copolymer-preferred according to the invention
AM: acrylamide,
ATBS: 2-acrylamido-2-methyl-propanesulfonic acid
MBA: N,N'-methylene-bis-acrylamide
TAA: triallylamine The amount of monomers (a) and (b) is given in [mole per mole of total monomer units] and the amount of the crosslinker in [mmoles per mole of total monomer units].

According to the results obtained and shown in table 1, the thickening properties of the water-swellable crosslinked copolymer according to the present invention (P1, P2) are significantly better (especially at acidic pH) than the examples X1, X2 and X3. It is to be noted that the best results are obtained by using the crosslinking agent TAA in an amount of 2.5 mmoles and by carrying out the polymerization at a pH of about 4. Furthermore, it is observed that the residual monomer content for the inventive examples is lower compared to examples X1, X2 and X3.

B) Compositions

The names of the ingredients used in the compositions are those given in the INCI (International Nomenclature of Cosmetic Ingredients).

Polymer "$P1_{dry}$" is the same polymer as polymer P1 but used in the form of a powder obtained by spray drying.

Example 1

Gel/Cream Base, pH 4.9

| | | Percent by weight: |
|---|---|---|
| Aqueous phase: | Glycerine | 2% |
| | Disodium EDTA | QS |
| | Water (aqua) | QSP 100 |
| | Citric acid | QS pH = 3.5 |
| Polymer P1 | | 3% |
| Preservatives | | QS |
| Fragrance + solubilizer | | QS |
| NaOH | | QS, final pH = 4.9 |

[QSP 100 = amount sufficient to make up 100 [%]]
[QS = sufficient amount]

Preparation Method:
First stage: preparation of the aqueous phase.
Second stage: adjustment of aqueous phase pH value by addition of acid.
Third stage: Polymer is added during agitation.
Fourth stage: preservatives and fragrance are added.
Fifth stage: readjustment of pH to 4.9

Example 2

Silicone-Based Lotion, pH 5.7

|  | Percent by weight: |
|---|---|
| cyclopentasiloxane | 6% |
| octyl palmitate | 5% |
| water (aqua) | QSP 100 |
| Polymer P1 | 3% |
| Preservatives | QS |

Preparation method: Mix Polymer P1 in cyclopentasiloxane, add premix in oil and then add aqueous phase in oil phase

Example 3

Hair Conditioner, pH 4

| Phase | | Percent per weight |
|---|---|---|
| A | Cyclomethicone | QSP 100 |
|  | Propylene Glycol | 30% |
|  | Fragrance | 0.3% |
| B | Water | QSP 100 |
| C | Polymer P1 | 2.5% |
| D | Acid Citric | QS pH = 4 |

Method of Preparation: Mix A, add premixed B, and add C until uniformity. Then, adjust the pH with D until pH=4.

Example 4

Oil/Water Makeup Removal Base, pH 4.7

|  |  | Percent by weight: |
|---|---|---|
| Aqueous phase: | Disodium laureth sulfosuccinate | 4% (active matter) |
|  | Glycerine | 3% |
|  | Water (aqua) | QSP 100 |
| Oily phase: | caprylic/capric triglyceride | 6% |
|  | soft almond oil (*Prunus Amigdalus Dulcia* ...) | 2% |
| Polymer P1 or P1$_{dry}$ |  | 4% |
| Preservatives |  | QS |
| Fragrance |  | QS |

Method of Preparation:
The aqueous phase is prepared. The oily phase is then incorporated. The polymer, then the preservatives and the fragrance are added during agitation.

Example 5

Oil/Water Emulsion Base

|  |  | Percent by weight: |
|---|---|---|
| Oily phase: | Shea butter" (*Butyrospermum Parkii*) (karate butter) | 2% |
|  | octyl stearate | 8% |
|  | mineral oil (paraffinum liquidum | 4% |

|  | Percent by weight: |
|---|---|
| Water (aqua) | QSP 100 |
| Polymer P1 | 2% |
| Preservatives | QS |
| Fragrance | QS |
| Citric acid | QS pH = 5.2 |

Method of Preparation:
Preparation of oily phase at 50° C. Oil is added in water and the temperature is held at 50° C. The polymer is added during agitation.
The mixture is then brought to ambient temperature in order to add the preservatives and the fragrance. The pH value is then set.

Example 6

Gel/Cream Base, pH 6

|  | Percent by weight: |
|---|---|
| water (aqua) < | QSP 100 |
| Polymer P1$_{dry}$ | 3% |
| NaOH | QS pH = 6 |
| Preservatives | QS |
| Fragrance | QS |

Method of Preparation:
Component A is poured into water. The pH value is set at 6. The preservatives and the fragrance and then added during agitation.

The examples presented in the foregoing demonstrate the variety of the compositions which may be targeted for use of this type of polymers, because of both their thickening and/or their emulsifying properties.

Each of the final compositions tested exhibits optimal cosmetic characteristics such as feel and stability. The feels resulting from the different formulations are oily: at the time of application, the texture of the inventive compositions or formulations "breaks down" more slowly, thus making it possible to avoid a feel which is too "watery" (one which resembles water), which holds little attraction for the consumer, especially in terms of efficiency and comfort of the composition.

This property also makes it possible to prevent the composition applied to the surface of the skin, hair, nails, hair, or body hairs from flowing out too quickly. Hence, it is easier to control application and spreading of the composition on the surface to be treated.

It has to be noted that there is a vast selection of packaging for each of the possible formulas: pump bottle, tube, spray, jar, etc.

In addition, it is shown herein that the use of a polymer in powder form represents an additional possibility. It permits the benefit of the properties of the polymer such as described above while preventing the presence of the oily phase (polymer solvent) in the final composition. This possibility allows for the provision of a variety of formulations or compositions meeting new technical and/or marketing demands.

The invention claimed is:
1. Polymeric thickener composition comprising at least one Water-swellable cross-linked copolymer derived from polymerization of a mixture having a pH of 3 to 5 consisting of:

(a) acrylamide,
(b) an acrylamidoalkylsulfonic acid and/or a salt thereof; and
(c) an amine-based polyfunctional crosslinking agent comprising at least three allylic functions, and a chain transfer agent, wherein the polyfunctional crosslinking agent is triallylamine and is contained in the polymerization mixture in an amount of more than 2 millimoles per mole of total monomer units and up to 10 millimoles per mole of total monomer units.

2. Polymeric thickener composition according to claim 1, wherein the acrylamidoalkylsulfonic salt is 2-acrylamido-2-methyl-propanesulfonic acid.

3. A cosmetic, dermatologic, pharmaceutical or veterinary water-containing formulation comprising the polymeric thickener composition according to claim 1.

4. The cosmetic, dermatologic, pharmaceutical or veterinary water-containing formulation according to claim 3, wherein the formulation has a pH value lower than 6 and contains silicone, vegetable oils, ingredients in saline form, salts or ingredients.

5. Polymeric thickener composition according to claim 1, wherein the acrylamidoalkylsulfonic salt is 2-acrylamido-2-methyl-propanesulfonic acid at least partially in the form of an ammonium salt and/or alkali metal salt.

6. Polymeric thickener composition according to claim 1, wherein the water-swellable crosslinked copolymer is prepared by inverse emulsion polymerization from a mixture consisting of (a) acrylamide, (b) an acrylamidoalkylsulfonic acid and/or a salt thereof and (c) an amine based polyfunctional crosslinking agent comprising at least three allylic functions, wherein the polyfunctional crosslinking agent is triallylamine and is added to the polymerization mixture in an amount of more than 2 millimoles per molecule of total monomer units and up to 10 millimoles per mole of total monomer units and wherein the polymerization is carried out at a pH of 3 to 5 in the presence of a transfer agent.

7. Polymer thickener composition according to claim 1, wherein an aqueous phase containing the (a) acrylamide and the (b) acrylamidoalkylsulfonic acid is dispersed in a hydrophobic phase.

8. Polymer thickener composition according to claim 1, wherein the pH value of the polymerization mixture is in the range between 3.5 and 4.5.

9. Polymer thickener composition according to claim 1, wherein the pH value of the polymerization mixture is about 4.

10. Polymer thickening composition according to claim 1, wherein the water-swellable crosslinked copolymer is isolated or obtained in solid form by precipitation of the polymerization product in a non-solvent medium, by azeotropic distillation in the presence of an agglomerating agent and a stabilizing polymer followed by filtration before drying of the obtained polymeric composition, by spray drying or by drying by atomization or pulverization.

11. Polymer thickener composition according to claim 1, wherein the chain transfer agent comprises a phosphate-type chain transfer agent, which is sodium hypophosphite, a lower alcohol, a thiol based chain transfer agent, which is 2-mercaptoethanol, a sulfate type chain transfer agent, which is sodium methallylsulfonate, or any mixture thereof.

12. Polymer thickener composition according to claim 11, wherein the lower alcohol is methanol or isopropanol.

13. Process for making a polymeric thickener according to claim 1, wherein the water-swellable cross-linked copolymer is prepared by inverse emulsion polymerization from a mixture consisting of (a) acrylamide, (b) an acrylamidoalkylsulfonic acid and/or a salt thereof and (c) an amine based polyfunctional crosslinking agent comprising at least three allylic functions, wherein the polyfunctional crosslinking agent is triallylamine and is added to the polymerization mixture in an amount of more than 2 millimoles per mole of total monomer and up to 10 millimoles per mole of total monomer units and wherein the polymerization is carried out at a pH of 3 to 5 in the presence of a transfer agent.

14. Process according to claim 13, wherein an aqueous phase containing the (a) acrylamide and the (b) acrylamidoalkylsulfonic acid is dispersed in a hydrophobic phase.

15. Process according to claim 13, wherein the pH value of the polymerization mixture is in the range between 3.5 and 4.5.

16. Process according to claim 13, wherein the water-swellable crosslinked copolymer is isolated or obtained in solid form by precipitation of the polymerization product in a non-solvent medium, by azeotropic distillation in the presence of an agglomerating agent and a stabilizing polymer followed by filtration before drying of the obtained polymeric composition, by spray drying or by drying by atomization or pulverization.

17. Polymeric thickener composition according to claim 13, wherein the water-swellable crosslinked copolymer is obtained or isolated in solid form.

18. Process according to claim 13, wherein the pH value of the polymerization mixture is about 4.

19. Polymer thickener composition according to claim 13, wherein the chain transfer agent comprises a phosphate-type chain transfer agent, which is sodium hypophosphite, a lower alcohol, a thiol based chain transfer agent, which is 2-mercaptoethanol, a sulfate type chain transfer agent, which is sodium methallylsulfonate, or any mixture thereof.

20. Polymer thickener composition according to claim 19, wherein the lower alcohol is methanol or isopropanol.

* * * * *